(12) United States Patent
Lee et al.

(10) Patent No.: US 7,671,088 B2
(45) Date of Patent: Mar. 2, 2010

(54) WATER-SOLUBLE ETOPOSIDE ANALOGS AND METHODS OF USE THEREOF

(75) Inventors: Kuo-Hsiung Lee, Chapel Hill, NC (US); Zhiyan Xiao, Chapel Hill, NC (US); Kenneth F. Bastow, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 335 days.

(21) Appl. No.: 11/619,304

(22) Filed: Jan. 3, 2007

(65) Prior Publication Data
US 2007/0123475 A1 May 31, 2007

Related U.S. Application Data

(60) Division of application No. 10/712,663, filed on Nov. 13, 2003, now Pat. No. 7,176,236, which is a continuation-in-part of application No. 10/349,351, filed on Jan. 22, 2003, now Pat. No. 6,872,841, which is a continuation of application No. 10/177,147, filed on Jun. 21, 2002, now Pat. No. 6,566,393.

(51) Int. Cl.
*A01N 43/26* (2006.01)
*A01N 43/00* (2006.01)
*A01N 43/04* (2006.01)
*A61K 31/335* (2006.01)
*A61K 31/33* (2006.01)
*C07D 307/77* (2006.01)
*C07D 307/00* (2006.01)
*C07D 317/00* (2006.01)
*C07D 323/02* (2006.01)

(52) U.S. Cl. .......................... 514/463; 514/183; 514/25; 549/298; 549/430

(58) Field of Classification Search .................. 514/463, 514/183, 25; 549/298, 430
See application file for complete search history.

(56) References Cited

U.S. PATENT DOCUMENTS

| | | | |
|---|---|---|---|
| 4,958,010 A | 9/1990 | Kadow et al. | |
| 5,132,322 A | 7/1992 | Lee et al. | |
| 5,300,500 A | 4/1994 | Lee et al. | |
| 5,332,811 A | 7/1994 | Lee et al. | |
| 5,338,867 A | 8/1994 | Choy et al. | |
| 5,541,223 A | 7/1996 | Lee et al. | |
| 5,571,914 A | 11/1996 | Terada et al. | |
| 6,281,198 B1 | 8/2001 | Monneret et al. | |
| 6,566,393 B1 | 5/2003 | Lee et al. | |

OTHER PUBLICATIONS

Ying-Jie, C et al., Synthesis and anticancer activity of new derivatives of podophyllotoxin, CA 130:296539 (1999).
Anyanwutaku, IO et al., Activities of novel nonglycosidic epipodophyllotoxins in etoposide-sensitive and -resistant variants of human KB cells, P-388 cells and in vivo multidrug-resistant murine leukemia cells, CA 124:331692 (1996).
Yan-Guang, W et al, Synthesis and anticancer activity of new derivatives of podophyllotoxin, CA 125:275518 (1996).
Cho, SJ et al, Antitumor agents. 163. Three-dimensional quantitative structure-activity relationship study of 4' -O-demethylepipodophyllotoxin analogs using the CoMFA/q2-GRS approach, CA 124:249647 (1996).
Kobayashi et al, Pharmacodynamics and long-term toxicity of Etoposide, PMID: 8070030.
Sinkule, Etoposide: a semisynthetic epipodophyllotoxin. Chemistry, pharmacology, pharmacokinetics, adverse effects and use as an antineoplastic agent. PMID: 6326063.
Atienza et al, Phase II study of oral Etoposide of patients with advanced breast cancer. PMID: 8625074.
Yasumizi, Clinical trial of daily low-dose oral etoposide for patients with residual or recurrent cancer of the ovary or uterus. PMID: 8640467 (1995).
Ajani, Oral etoposide for patients with metastatic gastric adenocarcinoma. PMID: 10198733 (1999).
International Search Report for PCT/US04/26475; Date of Mailing Jan. 31, 2005.
Xiao et al., *Antitumor Agents. 229. Design, Synthesis, and Biological Evaluation of Novel 4β-[4"- Benzamido)-Amino]-4'0'Demethyl-Epipodophyllotoxins and Related Derivatives*, Unpublished draft paper.

*Primary Examiner*—Shaojia Anna Jiang
*Assistant Examiner*—Scarlett Goon
(74) *Attorney, Agent, or Firm*—Myers Bigel Sibley & Sajovec, P.A.

(57) ABSTRACT

Etoposide analogs with improved water-solubility such as 4'-O-Demethyl-4'-(N',N'-dimethyl-glycyl)-4β-(4"-nitroanilino)-4-desoxy-podophyllotoxin (8) and 4'-O-Demethyl-4'-(N',N'-dimethyl-glycyl)-4β-(4"-fluoroanilino)-4-desoxy-podophyllotoxin (9) are described, along with pharmaceutical formulations containing the same, methods of use thereof, and intermediates and methods of making the same.

11 Claims, No Drawings

WATER-SOLUBLE ETOPOSIDE ANALOGS AND METHODS OF USE THEREOF

RELATED APPLICATIONS

This application claims priority to and is a divisional of U.S. patent application Ser. No. 10/712,663, filed Nov. 13, 2003, now issued as U.S. Pat. No. 7,176,236, which is a continuation-in-part of U.S. patent application Ser. No. 10/349,351, filed Jan. 22, 2003, now issued as U.S. Pat. No. 6,872,841, which in turn is a continuation of U.S. patent application Ser. No. 10/177,147, filed Jun. 21, 2002, now issued as U.S Pat. No. 6,566,393, the disclosures of all of which are incorporated by reference herein in their entirety.

STATEMENT OF GOVERNMENT SUPPORT

This invention was made with government support under NIH grant CA 17625-24. The Government has certain rights to this invention.

FIELD OF THE INVENTION

The present invention concerns water-soluble etoposide or podophyllotoxin analogs such as 4-beta-[(4"-benzamido)-amino]-4'-demethyl-epipodophyllotoxins and their 4'-ester derivatives, pharmnaceutical formulations containing the same, and the use thereof to treat cancer.

BACKGROUND OF THE INVENTION

Etoposide (1) and Teniposide (2) are semisynthetic glucosidic cyclic acetals of podophyllotoxin (3) currently used in the chemotherapy for various types of cancer

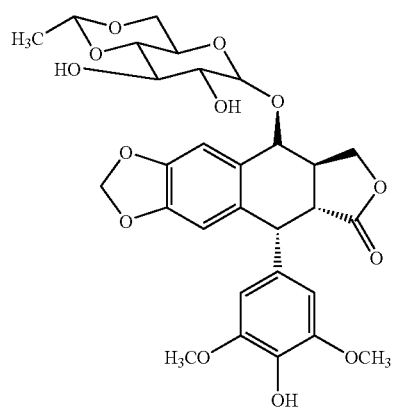

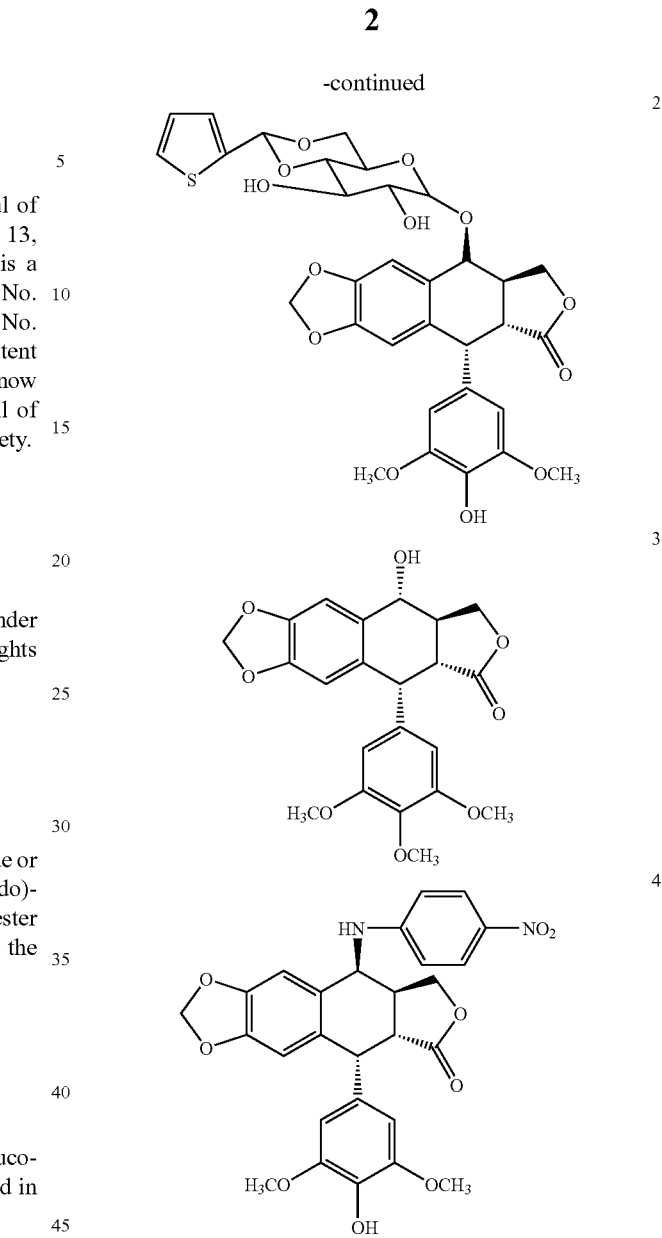

(Jardine. (1980) *Anticancer Agents Based on Natural Products Models*; Academic Press: New York, p. 319, Issell. (1982) *Cancer Chemother. Pharmacol.* 7:73). Another epipodophyllotoxin derivative, GL-331, has been developed and tested in phase II clinical trials against various cancers (Lee et al. (1995) *Food and Drug Analysis.* 3:209). Interestingly, although podophyllotoxin inhibits the assembly of microtubules, the primary action mode of its 4β-congeners, the epipodophyllotoxins, is to inhibit the catalytic activity of topoisomerase II by stabilizing the covalent topoisomerase II-DNA cleavable complex, cause DNA strands breaking and eventually lead to cell death (Osheroff et al. (1991) *BioEssays* 13:269, Alton & Harris (1993) *Br. J. Haematol.* 85:241-245, Cho et al. (1996) *J. Med. Chem.* 39:1383-1395, MacDonald et al. (1991) *DNA Topoisomerase in Cancer*; Oxford University Press: New York, p. 119).

Major problems associated with etoposide and teniposide include acquired drug-resistance and poor water-solubility. U.S. Pat. No. 6,566,393 to Lee et al. describes unique etoposide analogs such as 4-beta-[(4"-benzamido)-amino]-4'-demethyl-epipodophyllotoxins to potentially overcome the drug-resistance problem. There remains a need for new etoposide analogs with anticancer and antitumor activity and more importantly, with improved water-solubility.

SUMMARY OF THE INVENTION

A first aspect of the present invention is a compound according to Formula I:

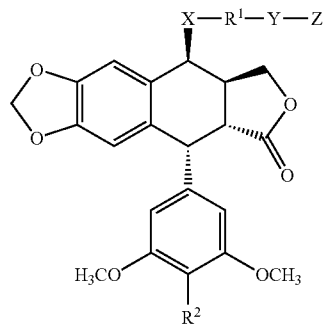

I wherein:

X is a linking group selected from the group consisting of —O—, —S—, —NH—, —CO—, —CH=N—, or $CH_2NH$—, and in one preferred embodiment is —NH—;

$R^1$ is a covalent linkage between X and Y, or is loweralkyl, loweralkenyl, or phenyl, and when phenyl is unsubstituted or is substituted from one to four times with loweralkyl, hydroxy, alkoxyl, alkylogen, or alkylamino, alkyoxycarbonyl, amino, halogen, nitro, or nitrile, and in one preferred embodiment $R^1$ is phenyl;

Y is none, —NHCO—, —CONH—, —OCO—, or —COO—;

Z is —$(CH_2)_nR_3$, where n is 0 to 8, and in which —$(CH_2)_n$— may be incorporated in Z as a five-, six-, seven-, or eight-membered rings, for example:

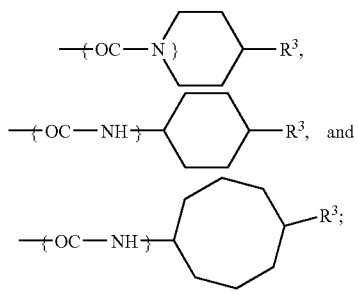

where the material in brackets represents group Y, and $R_3$ is a loweralkyl, loweralkenyl, aryl, lower alkylamino, lower alkenylamino, or arylamino;

$R^2$ is —$OR_4$, —$NR_4R_5$, —$OCOR_4$, —$OCOOR_4$, —$OCOSR_4$, or —$OCONR_4R_5$, where $R_4$ and $R_5$ are selected from lower alkylamino, lower alkenylamino, or arylamino;

or a pharmaceutically acceptable salt thereof.

A further aspect of the present invention is a pharmaceutical formulation comprising a compound as described above in a pharmaceutically acceptable carrier (e.g.,an aqueous carrier).

A still further aspect of the present invention is a method of treating a cancer, comprising administering to a human or animal subject in need thereof a treatment effective amount (e.g., an amount effective to treat, slow the progression of, etc.) of a compound as described above. Examples of cancers that may be treated include, but are not limited to, skin cancer, lung cancer including small cell lung cancer and non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

DETAILED DESCRIPTION OF THE INVENTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents and other references mentioned herein are incorporated by reference in their entirety.

The term "alkyl" or "loweralkyl" as used herein refers to C1 to C4, C6 or C8 alkyl, which may be linear or branched and saturated or unsaturated.

"Cycloalkyl" is specified as such herein, and is typically C3, C4 or C5 to C6 or C8 cycloalkyl.

"Alkenyl" or "loweralkenyl" as used herein likewise refers to C1 to C4 alkenyl, and alkoxy or loweralkoxy as used herein likewise refers to C1 to C4 alkoxy.

"Alkoxy" as used herein refers to linear or branched, saturated or unsaturated oxo-hydrocarbon chains, including for example methoxy, ethoxy, propoxy, isopropoxy, butoxy, and t-butoxy.

"Alkylogen" as used herein means alkyl or loweralkyl in which one, two, three or more (e.g., all) hydrogens thereon have been replaced with halo. Examples of alkylogen include but are not limited to trifluoromethyl, chloromethyl, 2-chloroethyl, 2-bromoethyl, and 2-iodoethyl. Alkylogens may also be referred to as haloalkyl or perhaloalkyl (e.g. fluoroalkyl; perfluoroalkyl).

The term "aryl" as used herein refers to C3 to C10 cyclic aromatic groups such as phenyl, naphthyl, and the like, and includes substituted aryl groups such as tolyl.

"Halo" as used herein refers to any halogen group, such as chloro, fluoro, bromo, or iodo.

The term "hydroxyalkyl" as used herein refers to C1 to C4 linear or branched hydroxy-substituted alkyl, i.e., —$CH_2OH$, —$(CH_2)_2OH$, etc.

The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —$NH_2$, —$NHCH_3$, —$N(CH_3)_2$, etc.

The term "oxyalkyl" as used herein refers to C1 to C4 oxygen-substituted alkayl, i.e., —OCH₃, and the term "oxyaryl" as used herein refers to C3 to C10 oxygen-substituted cyclic aromatic groups.

The term "alkylenedioxy" refers to a group of the general formula —OR'O—, —OR'OR'—, or —R'OR'OR'— where each R' is independently alkyl.

"Treat" or "treating" as used herein refers to any type of treatment that imparts a benefit to a patient afflicted with a disease, including improvement in the condition of the patient (e.g., in one or more symptoms), delay in the progression of the disease, prevention or delay of the onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein means that a potential effect is partially or completely eliminated.

The present invention is concerned primarily with the treatment of human subjects, but may also be employed for the treatment of other animal subjects (i.e., mammals such as dogs, cats, horses, etc. or avians) for veterinary purposes. Mammals are preferred, with humans being particularly preferred.

A. Active Compounds.

Active compounds of the present invention may be produced by the procedures described herein or variations thereof which will be apparent to those skilled in the art. Novel methods useful for producing active compounds included herein are also an aspect of the present invention.

U.S. Pat. No. 6,566,393 to Lee et al. describes the general synthetic methods for C4 side chain extension and synthetic methods for C4' side chain addition are described below is as follows:

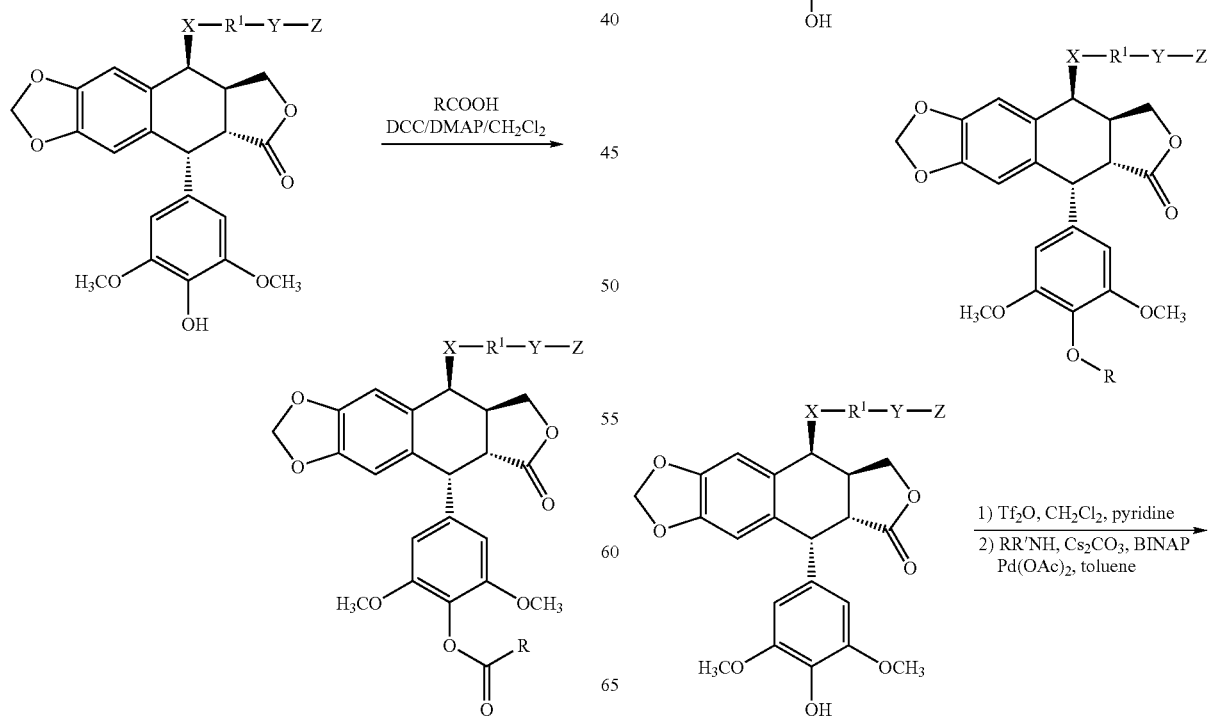

-continued

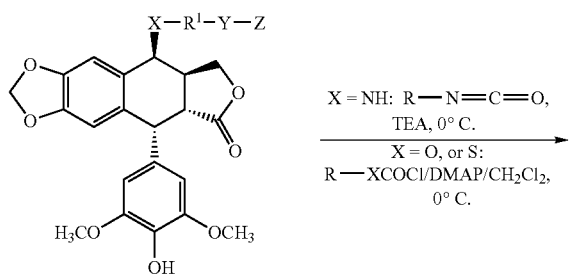

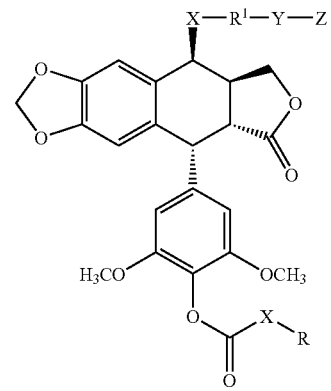

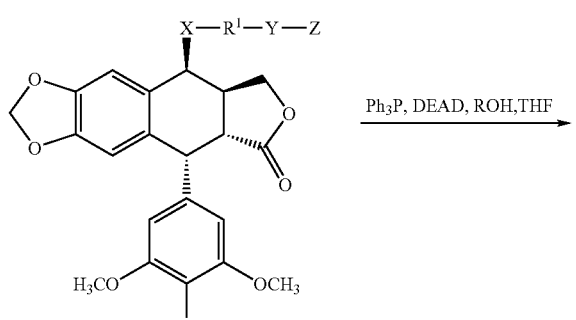

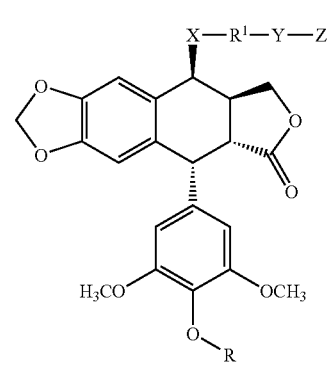

-continued

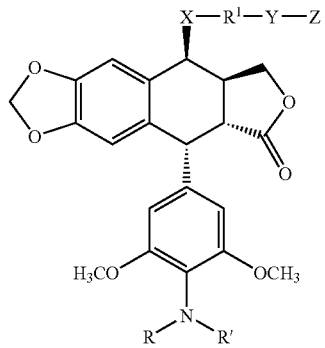

Compounds of Formula I as noted above can be produced in the manner described above, or modifications thereof which will be apparent to those skilled in the art. Particularly preferred embodiments of the present invention are: (i) compounds of Formula IIa:

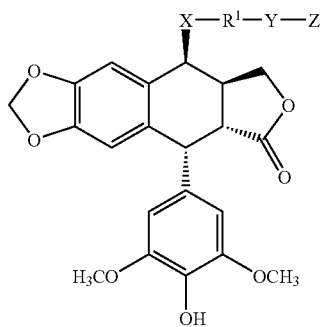

wherein:

X is a linking group selected from the group consisting of —O—, —S—, —NH—, —CO—, —CH=N—, and CH$_2$NH—;

R$^1$ is a covalent linkage between X and Y, or is loweralkyl, loweralkenyl, or phenyl, and when phenyl is unsubstituted or is substituted from one to four times with loweralkyl, hydroxy, alkoxyl, alkylogen, alkylamino, alkyoxycarbonyl, amino, halogen, nitro, or nitrile;

Y is none, —NHCO—, —CONH—, —OCO—, or —COO—;

Z is —CHR$^2$(CH$_2$)$_n$R$^3$, where n is 0 to 8, or —(CH$_2$)$_n$— is incorporated into Z as a five-, six-, seven-, or eight-membered ring; R$^2$ is H, and R$^3$ is a loweralkyl, loweralkenyl, aryl, lower alkylamino, lower alkenylamino, or arylamino;

or a pharmaceutically acceptable salt thereof; or
(ii) compounds of Formula IIb:

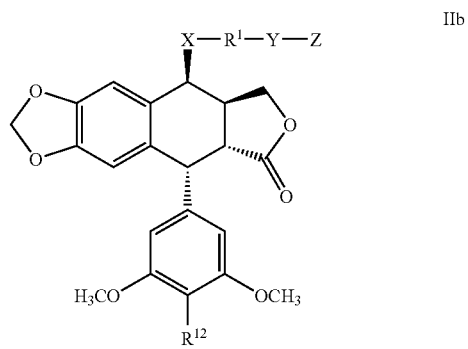

wherein:

X is a linking group selected from the group consisting of —O—, —S—, —NH—, —CO—, —CH=N—, or CH$_2$NH—, and in one preferred embodiment is —NH—;

R$^1$ is a covalent linkage between X and Z, or is loweralkyl, loweralkenyl, or phenyl, and when phenyl is unsubstituted or is substituted from one to four times with loweralkyl, hydroxy, alkoxyl, alkylogen, alkylamino, alkyoxycarbonyl, amino, halogen, nitro, or nitrile;

Y is none, —NHCO—, —CONH—, —OCO—, or —COO—;

Z is —(CH$_2$)$_n$R$^3$, where n is 0 to 8, or —(CH$_2$)$_n$— is incorporated into Z as a five-, six-, seven-, or eight-membered ring, R$^3$ is a loweralkyl, loweralkenyl, aryl, lower alkylamino, lower alkenylamino, or arylamino;

R$^{12}$ is —OR$_4$, —NR$_4$R$_5$, —OCOR$_4$, —OCOOR$_4$, —OCOSR$_4$, or —OCONR$_4$R$_5$, where R$_4$ and R$_5$ are selected from the group consisting of lower alkylamino, lower alkenylamino, and arylamino;

or a pharmaceutically acceptable salt thereof.

Note that an important feature of compounds of Formula IIa above is that, in substituent Z, R$^2$ is H. Note that an important feature of compounds of Formula IIb above is the group R$^{12}$ at the c4' position. In both compounds of Formula IIa and IIb, R$^1$ is preferably phenyl, X is preferably —NH—, and Y is prefereably —CONH—. R$^{12}$ is preferably —OCOCH$_2$N(CH$_3$)$_2$.

Examples of active compounds of the present invention that can be produced by the procedures described above include, but are not limited to:

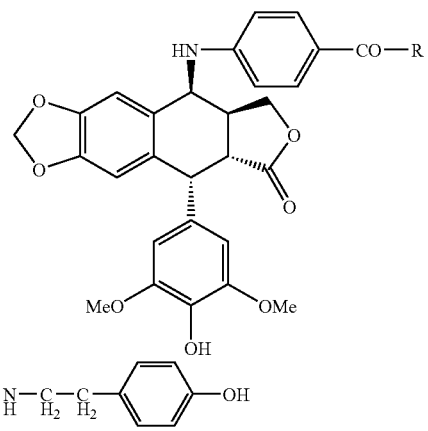

9

4'-O-Demethyl-4β-[4''(tyramido)-anilino]-4-desoxy-podophyllotoxin

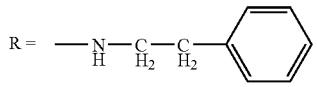

4'-O-Demethyl-4β-[4''-(phenylethylamido)-anilino]-4-desoxy-podophyllotoxin

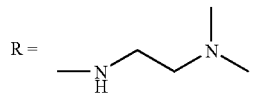

4'-O-Demethyl-4β-{[4''-(2'''-dimethylamino)-ethylamido]-anilino}-4-desoxy-podophyllotoxin

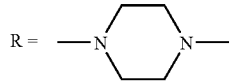

4'-O-Demethyl-4β-{[4''-(4'''-methyl-piperazyl)-amido]-anilino}-4-desoxy-podophyllotoxin

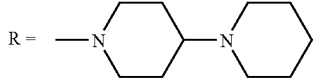

4'-O-Demethyl-4β-{[4''-(4'''-piperidinopiperidyl)-amido]-anilino}-4-desoxy-podophyllotoxin

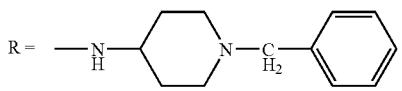

4'-O-Demethyl-4β-{[4''-N-(4'''-amino-1'''-benzylpiperidine)-amido]-anilino}-4-desoxy-podophyllotoxin

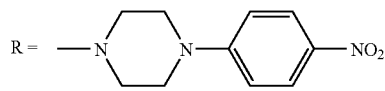

10

4'-O-Demethyl-4β-{[4''-(4'''-nitrophenyl-piperazyl)-amido]-anilino}-4-desoxy-podophyllotoxin

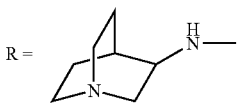

4'-O-Demethyl-4β-{[4''-N-(3'''-aminoquinuclidine)-amido]-anilino}-4-desoxy-podophyllotoxin

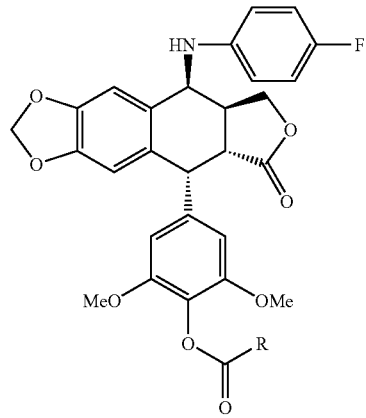

4'-O-Demethyl-4'-(N',N'-dimethyl-glycyl)-4β-(4''-fluoroanilino)-4-desoxy-podophyllotoxin

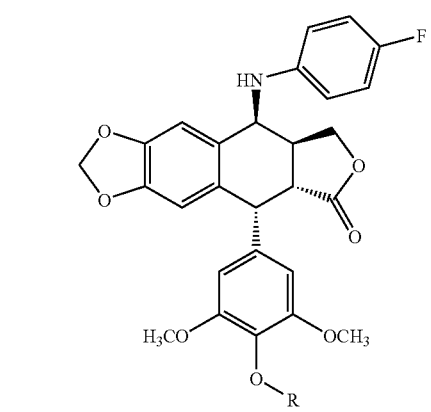

4'-O-Demethyl-4'-[(2'''-dimethylamino)-ethoxyl]-4β-(4''-fluoroanilino)-4-desoxy-podophyllotoxin 4'-O-Demethyl-4'-[(2'''-dimethylamino)-ethylamino]-4β-(4''-fluoroanilino)-4-desoxy-podophyllotoxin B. Formulations and Pharmaceutically Acceptable Salts.

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

The compounds of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3:318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

C. Methods of Use.

In addition to the compounds of the formulas described herein, the present invention also provides useful therapeutic methods. For example, the present invention provides a method of inducing cytotoxicity against tumor cells, or treating a cancer or tumor in a subject in need thereof.

Cancer cells which may be inhibited include cells from skin cancer, small cell lung cancer, non-small cell lung cancer, testicular cancer, lymphoma, leukemia, Kaposi's sarcoma, esophageal cancer, stomach cancer, colon cancer, breast cancer, endometrial cancer, ovarian cancer, central nervous system cancer, liver cancer and prostate cancer.

Subjects which may be treated using the methods of the present invention are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising the compounds of formulae described herein, or pharmaceutically acceptable salts thereof, in pharmaceutically acceptable carriers for any suitable route of administration, including but not limited to oral, rectal, topical, buccal, parenteral, intramuscular, intradermal, intravenous, and transdermnal administration.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

The present invention is explained in greater detail in the following non-limiting examples.

EXAMPLE 1

Experimental. The compounds 5-6 were synthesized from podophyllotoxin (3) as outlined in Scheme 1 according to previous published methods. 4'-demethyl-epipodophyllotoxin (DMEP) was synthesized from podophyllotoxin stereoselectively using the methanesulphonic acid/sodium iodide reagents (Kamal et al. (2000) *Bioorg Med. Chem. Lett.* 10:2059) followed by nucleophilic substitution with water. This intermediate was subjected to nucleophilic displacement by 4-amino benzoic acid to afford intermediate 7. Compounds 5 and 6 were synthesized from condensation of 7 with the corresponding amines by employing reagents dicyclohexylcarbodiimide (DCC) and 4-(dimethylamino) pyridine (DMAP).

The compounds 9-14 were synthesized from 4β-arylamino-podophyllotoxin derivatives with simple esterification in the presence of DCC and DMAP.

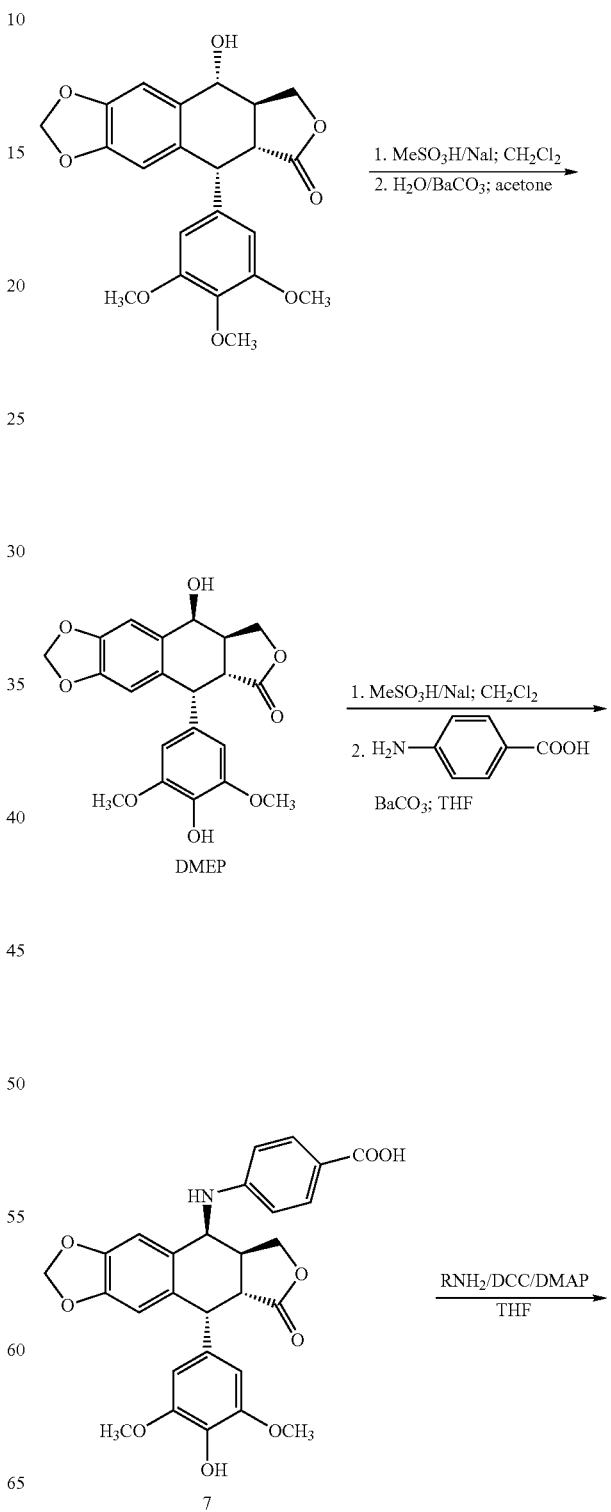

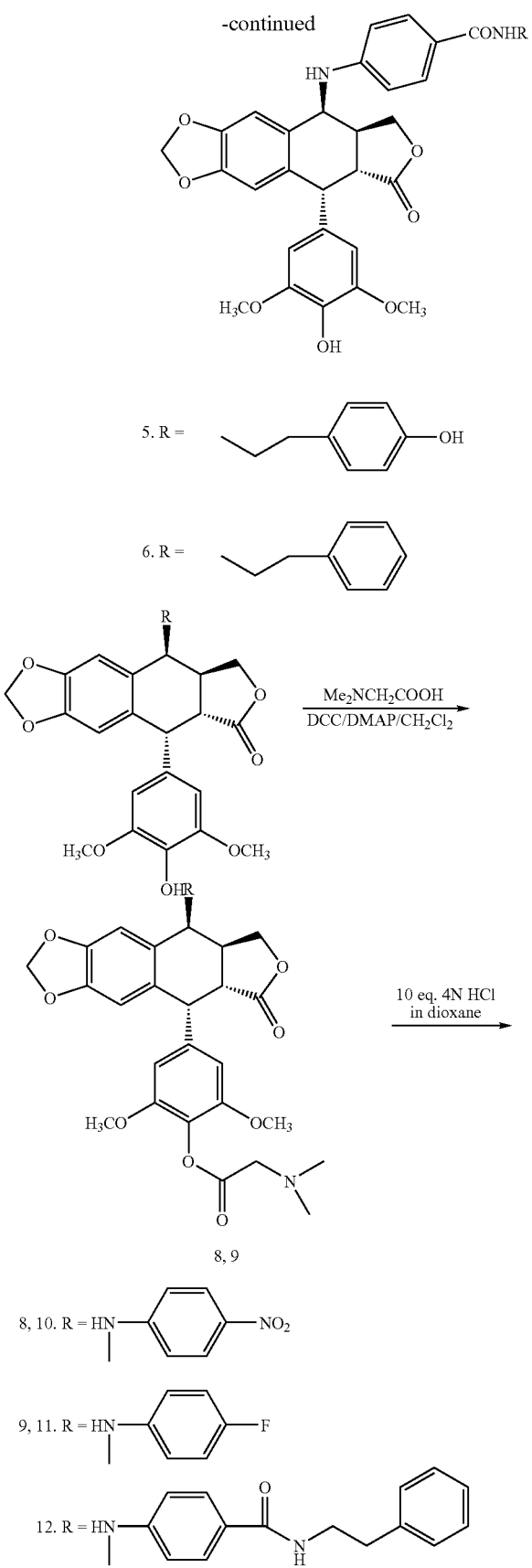
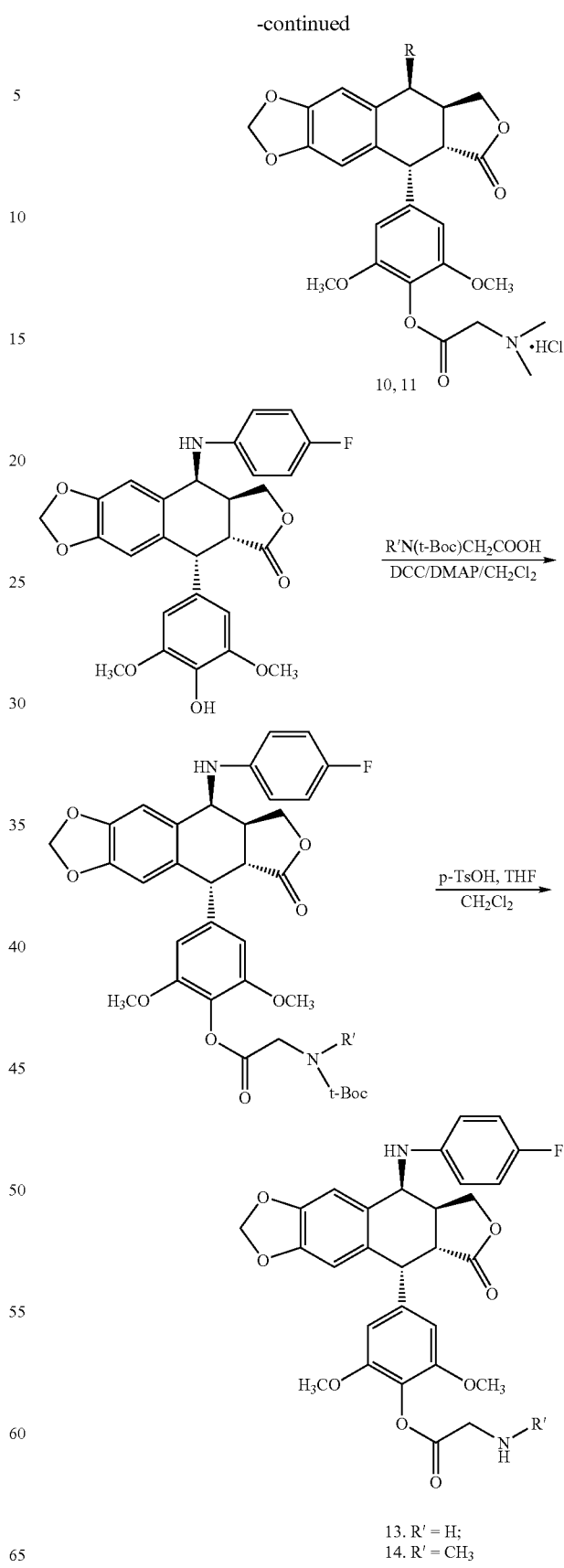

All melting points were taken on Fisher-Johns and Mel-Temp II melting point instruments and are uncorrected. IR spectra were recorded on a Perkin-Elmer 1320 spectrophotometer. $^1$H NMR spectra were obtained using Bruker AC-300 and WM 250 NMR spectrometers with TMS as the internal standard. All chemical shifts are reported in ppm. FABMS and HRFABMS spectral analyses were determined on a JOEL HX-110 instrument. Analytical thin-layer chromatography (TLC) was carried out on Merck precoated aluminum silica gel sheets (Kieselgel 60 F-254). Optical rotations were measured with a JASCO DIP-1000 polarimeter. All target compounds were characterized by $^1$H and IR spectral analyses and MS analyses.

EXAMPLE 2

General Preparation of 4'-demethyl-desoxypodophyllotoxins (5-6). To a solution of 7 (0.1 mmol) in tetrahydrofuran (3 ml) was added dicyclohexylcarbodiimide (DCC, 22 mg, 0.11 mmol). After 15 minutes, an appropriate amine (0.1 mmol) was added to the reaction mixture and the mixture was stirred at ambient temperature overnight. The suspension was diluted with 10 ml EtOAc and was filtered. After the solvent was removed under reduced pressure, the crude product was chromatographed on the FlahElute system using a 12M silica cartridge and the elute solvent: EtOAc: hexanes 1:1.

4'-O-Demethyl-4β-[4"(tyramido)-anilino]-4-desoxy-podophyllotoxin (5): yield 82%; mp 173-175° C.; $[\alpha]^{25}_D$-103.0 (c=0.1, acetone); IR (film) 1767 (lactone), 1695 (amide), 1470, 1448, 1382 (aromatic C=C), 1122 (phenol) cm$^{-1}$; MS m/e: 638 [M]$^+$; $^1$H NMR (acetone-d$_6$) δ 7.72 (d, J=8.7 Hz, 2H, 3", 5"-H), 7.07 (d, J=8.7 Hz, 2H, 2''', 6'''H), 6.84 (s, 1H, 5-H), 6.78 (d, J=8.7 Hz, 2H, 2", 6"-H), 6.76 (d, J=8.7 Hz, 2H, 3''', 5'''-H), 6.54 (s, 1H, 8-H), 6.39 (s, 2H, 2', 6'-H), 5.98 (dd, J=2.4, 0.9 Hz, 2 H, —OCH$_2$O—), 5.06 (m, 1H, 1-H), 4.60 (d, J=4.5 Hz, 1H, 4-H), 4.40 (t, J=7.8 Hz, 1 H, 11-H), 3.85 (t, J=7.8 Hz, 1H, 11-H), 3.70 (s, 6H, 3',5'-OCH$_3$), 3.50 (m, 2H, —NH—CH$_2$—), 3.26 (m, 2H, 2, 3-H), 2.79 (t, J=7.8 Hz, 2H, —CH$_2$-Ph-). Anal. (C$_{36}$H$_{34}$N$_2$O$_9$.2.1/4H$_2$O) C, H, N.

4'-O-Demethyl-4β-[4"-(phenylethylamido)-anilino]-4-desoxy-podophyllotoxin (6): yield 84%; mp 166-167° C.; $[\alpha]^{25}_D$-96.0 (c=0.1, acetone); IR (film) 1732 (lactone), 1463 (aromatic C=C), 1120 (phenol) MS m/e: 621 [M--1]$^+$; $^1$H NMR (CDCl$_3$) δ 7.50 (d, J=8.4 Hz, 2H, 3", 5"-H), 7.25-7.12 (m, 5H, 2'''-6'''H), 6.67 (s, 1 H, 5-H), 6.44 (d, J=8.4 Hz, 2H, 2", 6"-H), 6.41 (s, 1H, 8-H), 6.23 (s, 2H, 2', 6'-H), 5.84 (dd, J=11.4, 0.9 Hz, 2H, —OCH$_2$O—), 4.65 (d, J=3.3 Hz, 1H, 1-H), 4.45 (d, J=4.2 Hz, 1H, 4-H), 4.22 (t, J=7.5 Hz, 1H, 11-H), 3.78 (t, J=3.9 Hz, 1H, 11-H), 3.65 (s, 6H, 3', 5'-OCH$_3$), 3.55 (m, 2H, —NH—CH$_2$—), 3.08-2.90 (m, 2H, 2, 3-H), 2.82 (t, J=6.9 Hz, 2H, —CH$_2$-Ph). Anal. (C$_{36}$H$_{34}$N$_2$O$_8$.2H$_2$O) C, H, N.

General Preparation of 4'-demethyl-desoxypodophyllotoxins (8-14). To a solution of appropriate arylamino-podophyllotoxin derivatives (0.2 mmol) in dichloromethane (10 ml) were added DCC (62 mg, 0.3 mmol), DMAP (24 mg, 0.2 mmol) and the corresponding carbonylic acids (0.3 mmol). The reaction mixture was stirred under nitrocen at room temperature for 24 h. Then, the suspension was filtered, concentrated, and purified with the FlashElute system using EtOAc: hexanes : Et$_3$N as eluant. The hydrochloride salts were obtained by treating the amines with 4.0 N hydrogen chloride in dioxane. Primary and secondary amines were afforded by deprotection with p-TsOH in CH$_2$Cl$_2$.

4'-O-Demethyl-4'-(N',N'-dimethyl-glycyl)-4β-(4"-nitroanilino)-4-desoxy-podophyllotoxin (8): yield 90%; mp 179-180° C.; $[\alpha]^{25}_D$-252.0 (c=0.05, acetone); IR (film) 1740 (lactone) 1719 (ester) 1455, 1369, 1365 (aromatic C=C) cm$^-$; MS m/e: 605 [M–1]$^+$; $^1$H NMR (CDCl$_3$) δ 8.11 (d, J=9.3 Hz, 2H, 3", 5"-H), 6.74 (s, 1H, 5-H), 6.56 (d, J=9.0 Hz, 2H, 2", 6"-H), 6.53 (s, 1H, 8-H), 6.32 (s, 2H, 2', 6'-H), 5.95 (dd, J=4.8, 1.5 Hz, 2H, —OCH$_2$O—), 4.79 (m, 1H, 1-H), 4.68 (d, J=4.8 Hz, 1H, 4-H), 4.38 (m, 1H, 11-H), 3.79 (m, 1H, 11-H), 3.67 (s, 6H, 3', 5'-OCH$_3$), 3.45 (s, 2H, —CO—CH$_2$—), 2.41 (s, 6H, —N(CH$_3$)$_2$).

4'-O-Demethyl-4'-(N',N'-dimethyl-glycyl)-4β-(4"-fluoroanilino)-4-desoxy-podophyllotoxin (9): yield % 84%; mp 127-129° C.; $[\alpha]^{25}_D$-101.0 (c=0.1, acetone); IR (film) 1742 (lactone) 1376, 1365 (aromatic C=C) cm$^{31\ 1}$; MS m/e: 577 [M–1]$^+$; $^1$H NMR (acetone-d$_6$) δ 6.94 (dd, J=8.7, 8.7 Hz, 2H, 3", 5"-H), 6.82 (s, 1H, 5-H), 6.75 (dd, J=9.0, 4.5 Hz, 2H, 2", 6"-H), 6.55 (s, 1H, 8-H), 6.47 (s, 2H, 2', 6'-H), 5.97 (dd, J=6.9, 1.0 Hz, 2H, —OCH$_2$O—), 4.91 (m, 1H, 1-H), 4.64 (d, J=4.8 Hz, 1H, 4-H), 4.42 (t,J=7.2 Hz, 1H, 11-H), 3.92 (t, J=7.2 Hz, 1H, 11-H), 3.68 (s, 6H, 3', 5'-OCH$_3$), 3.39 (s, 2H, —CO—CH$_2$—), 3.32 (m, 1H, 2-H), 3.18 (m, 1H, 3-H), 2.35 (s, 6H, —N(CH$_3$)$_2$).

4'-O-Demethyl-4'-(N',N'-dimethyl-glycyl)-4β-(4"-nitroanilino)-4-desoxy-podophyllotoxin hydrochloride (10): yield 92%; mp 201-202° C.; $[\alpha]^{25}_D$-118.0 (c=0.2, acetone); IR (film) 1740 (lactone) 1369, 1365 (aromatic C=C) cm$^{-1}$; $^1$H NMR (CD$_3$OD) δ 8.11 (d, J=9.3 Hz, 2H, 3", 5"-H), 6.77 (s, 1H, 5-H), 6.72 (d, J=9.3 Hz, 2H, 2", 6"-H), 6.54 (s, 1H, 8-H), 6.46 (s, 2H, 2', 6'-H), 5.94 (d, J=4.5 Hz, 2H, —OCH$_2$O—), 4.89 (m, 1H, 1-H), 4.68 (d, J=4.8 Hz, 1H, 4-H), 4.36 (m, 1H, 11-H), 3.74 (m, 1H, 11-H), 3.71 (s, 2H, —CO—CH$_2$—), 3.66 (s, 6H, 3', 5'-OCH$_3$), 3.29 (m, 2 H, 2, 3-H), 2.92 (s, 6H, —N(CH$_3$)$_2$).

4'-O-Demethyl-4'-(N',N'-dimethyl-glycyl)-4β-(4"-fluoroanilino)-4-desoxy- podophyllotoxin hydrochloride (11): yield 97%; mp 162-163° C.; $[\alpha]^{25}_D$-117.0 (c=0.05, acetone); IR (film) 1738 (lactone) 1373, 1365 (aromatic C=C) cm$^{-1}$; $^1$H NMR (CD$_3$OD) δ 6.83 (dd, J=8.7, 8.7 Hz, 2H, 3", 5"-H), 6.68 (s, 1H, 5-H), 6.58 (dd, J=9.0, 4.5 Hz, 2H, 2", 6"-H), 6.44 (s, 1H, 8-H), 6.40 (s, 2H, 2', 6'-H), 5.86 (d, J=7.8 Hz, 2H, —OCH$_2$O—), 4.72 (m, 1H, 1-H), 4.63 (d, J=4.8 Hz, 1H, 4-H), 4.35 (t, J=7.2 Hz, 1H, 11-H), 3.88 (t, J=7.2 Hz, 1H, 11-H), 3.65 (s, 6H, 3', 5'-OCH$_3$), 3.59 (s, 2 H, —CO—CH$_2$—), 3.30 (m, 2H, 2, 3-H), 2.98 (s, 6H, —N(CH$_3$)$_2$).

4'-O-Demethyl-4'-glycyl-4β-(4"-fluoroanilino)-4-desoxy-podophyllotoxin (13): yield % 25% (from NPF); mp 133-135° C.; $[\alpha]^{25}_D$-69.0 (c=0.1, acetone); IR (film) 1740 (lactone) 1378, 1365 (aromatic C=C) cm$^-$; MS m/e: 549 [M–1]$^+$; $^1$H NMR (CD$_3$OD) δ 6.89 (dd, J=8.7, 8.7 Hz, 2H, 3", 5"-H), 6.75 (s, 1H, 5-H), 6.63 (dd, J=9.0, 4.5 Hz, 2H, 2", 6"-H), 6.51 (s, 1H, 8-H), 6.44 (s, 2H, 2', 6'-H), 5.92 (d, J=4.5 Hz, 2H, —OCH$_2$O—), 4.67 (m, 1H, 1-H), 4.53 (d, J=4.5 Hz, 1H, 4-H), 4.41 (m, 1H, 11-H), 3.90 (m, 1H, 11-H), 3.69 (s, 6H, 3', 5'-OCH$_3$), 3.30 (s, 2H, —CO—CH$_2$—), 3.28 (m, 1H, 2-H), 3.08 (m, 1H, 3-H).

4'-O-Demethyl-4'-sarcrosyl-4β-(4"-fluoroanilino)-4-desoxy-podophyllotoxin (14): yield % 38% (from NPF); mp 138-139° C.; $[\alpha]^{25}_D$-104.0 (c=0.2, acetone); IR (film) 1734 (lactone) 1457, 1365 (aromatic C=C) cm$^{-1}$; MS m/e: 563 [M–1]$^+$; $^1$H NMR (CD$_3$OD) δ 6.90 (dd, J=8.7, 8.7 Hz, 2H, 3", 5"-H), 6.73 (s, 1H, 5-H), 6.63 (dd, J=8.7, 4.5 Hz, 2H, 2", 6"-H), 6.48 (s, 1H, 8-H), 6.35 (s, 2H, 2', 6'-H), 5.92 (dd, J=4.5, 1.5 Hz, 2H, —OCH$_2$O—), 4.75 (d, J=4.2 Hz, 1H, 1-H), 4.56 (d, J=4.8 Hz, 1H, 4-H), 4.39 (t, J=7.2 Hz, 1H, 11-H), 3.90 (t, J=7.2 Hz, 1H, 11-H), 3.70 (s, 6H, 3', 5'-OCH$_3$), 3.31 (s, 2H, —CO—CH$_2$—), 3.16 (m, 1H, 2-H), 3.09 (m, 1H, 3-H), 2.43 (s, 3 H, —NH(CH$_3$)).

EXAMPLE 3

Biological Assay and Results. The compounds 5-6, 8-14 were evaluated for their inhibition against KB and 1-resistant KB-7d cells and ability to induce cellular protein-linked DNA breaks (PLDB) (Table 1). Most compounds effectively inhibited the KB cell growth, and more notably, retained the inhibition against the 1-resistant KB-7d cells.

TABLE 1

Induction of protein-linked DNA breaks and inhibition of tumor cells by 5-6 and 8-14.

| Comp. | R | R' | % PLDB formation[a] | KB ED$_{50}$[b] (μg/ml) | KB-7d ED$_{50}$[b] (μg/ml) |
|---|---|---|---|---|---|
| 1 | (sugar: 4,6-O-ethylidene-β-D-glucopyranosyl) | H | 100 | 0.5 | >10 |
| 4 | HN–C$_6$H$_4$–NO$_2$ (para) | H | 228 | 0.33 | 2 |
| 5 | HN(CH$_3$)–C$_6$H$_4$–CO–NH–CH$_2$CH$_2$–C$_6$H$_4$–OH | H | 275 | 0.025 | 0.8 |
| 6 | HN(CH$_3$)–C$_6$H$_4$–CO–NH–CH$_2$CH$_2$–C$_6$H$_5$ | H | 227 | 0.035 | 0.5 |
| 8 | HN–C$_6$H$_4$–NO$_2$ | –C(O)CH$_2$N(CH$_3$)$_2$ | 219 | 0.4 | 8 |
| 9 | HN–C$_6$H$_4$–F | –C(O)CH$_2$N(CH$_3$)$_2$ | 165 | 0.4 | 8.0 |
| 10 | HN–C$_6$H$_4$–NO$_2$ | –C(O)CH$_2$N(CH$_3$)$_2$ | 156 | 2 | 10 |
| 11 | HN–C$_6$H$_4$–F | –C(O)CH$_2$N(CH$_3$)$_2$ | 102 | 0.9 | 10 |
| 12 | HN(CH$_3$)–C$_6$H$_4$–CO–NH–CH$_2$CH$_2$–C$_6$H$_5$ | –C(O)CH$_2$N(CH$_3$)$_2$ | 161 | 0.2 | 2 |
| 13 | HN–C$_6$H$_4$–F | –C(O)CH$_2$NH$_2$ | 199 | 0.35 | 10 |

TABLE 1-continued

Induction of protein-linked DNA breaks and inhibition of tumor cells by 5-6 and 8-14.

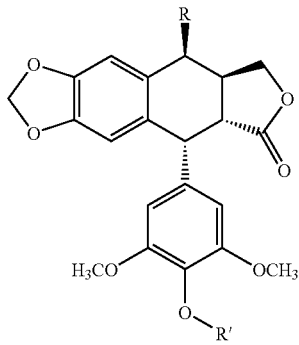

| Comp. | R | R' | % PLDB formation[a] | KB ED$_{50}$[b] (μg/ml) | KB-7d ED$_{50}$[b] (μg/ml) |
|---|---|---|---|---|---|
| 14 | 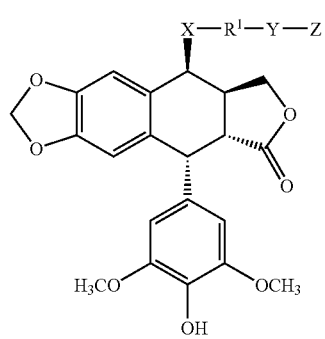 |  | 172 | 1 | 9 |

[a]% PLDB formation was determined by the SDS/potassium precipitation method. Percentage values were levels of protein-linked DNA breaks induced by drug treatment relative to the VP-16 control set arbitrarily at 100%. The values reflected effects at the concentration of 5 μg/ml.
[b]ED$_{50}$ was the concentration of drug that afforded 50% reduction in cell number after a 3-day incubation.

The foregoing is illustrative of the present invention, and is not to be construed as limiting thereof. The invention is defined by the following claims, with equivalents of the claims to be included therein.

What is claimed is:
1. A compound of Formula (IIa):

(IIa)

wherein:
X is a linking group selected from the group consisting of —O—, —S—, —NH—, —CO—, —CH=N—, and CH$_2$NH—;
R$^1$ is phenyl, which phenyl is unsubstituted or is substituted from one to four times with loweralkyl, hydroxy, alkoxyl, alkylogen, alkylamino, alkyoxycarbonyl, amino, halogen, nitro, or nitrile;
Y is none, —NHCO—, —CONH—, or —OCO;
Z is —CHR$^2$(CH$_2$)$_n$R$^3$, where n is 0 to 8, or —(CH$_2$)$_n$— is incorporated into Z as a five-, six-, seven-, or eight-membered ring; R$^2$ is H, and R$^3$ is a loweralkyl, loweralkenyl, aryl, lower alkylamino, lower alkenylamino, or arylamino;
or a pharmaceutically acceptable salt thereof.

2. A compound according to claim 1, wherein X is —NH—.

3. A pharmaceutical formulation comprising a compound according to claim 1 in a pharmaceutically acceptable carrier.

4. The pharmaceutical formulation according to claim 3, wherein said carrier is an aqueous carrier.

5. A method of treating a subject afflicted with a cancer, comprising administering to a subject in need thereof a treatment effective amount of a compound according to claim 1, wherein said cancer is selected from the group consisting of skin cancer, lung cancer, Kaposi's sarcoma, testicular cancer, lymphoma, leukemia, esophageal cancer, stomach cancer, colon cancer, breast cancer, endometrial cancer, ovarian cancer, central nervous system cancer, liver cancer and prostate cancer.

6. The method according to claim 5, wherein said cancer is prostate cancer.

7. The method according to claim 5, wherein said cancer is colon cancer.

8. The method according to claim 5, wherein said cancer is lung cancer.

9. The method according to claim 5, wherein said cancer is breast cancer.

10. The method according to claim 5, wherein X is —NH—.

11. The compound claim 1, wherein:
X is NH; and
Y is —CONH—.

* * * * *

UNITED STATES PATENT AND TRADEMARK OFFICE
CERTIFICATE OF CORRECTION

PATENT NO. : 7,671,088 B2  Page 1 of 1
APPLICATION NO. : 11/619304
DATED : March 2, 2010
INVENTOR(S) : Lee et al.

It is certified that error appears in the above-identified patent and that said Letters Patent is hereby corrected as shown below:

Column 20, Table 1, Item 10: Please correct

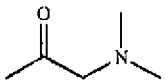

To read:

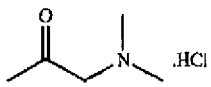

Column 20, Table 1, Item 11: Please correct

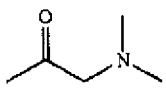

To read:

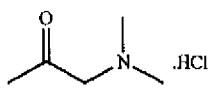

Signed and Sealed this

Twenty-seventh Day of July, 2010

David J. Kappos
*Director of the United States Patent and Trademark Office*